United States Patent [19]

Alfano et al.

[11] Patent Number: 5,847,394
[45] Date of Patent: *Dec. 8, 1998

[54] IMAGING OF OBJECTS BASED UPON THE POLARIZATION OR DEPOLARIZATION OF LIGHT

[75] Inventors: Robert R. Alfano, Bronx; Stavros G. Demos, Astoria, both of N.Y.

[73] Assignee: Research Foundation of City College of New York

[*] Notice: The term of this patent shall not extend beyond the expiration date of Pat. No. 5,719,399.

[21] Appl. No.: 704,841

[22] Filed: Aug. 28, 1996

Related U.S. Application Data

[63] Continuation-in-part of Ser. No. 573,939, Dec. 18, 1995, Pat. No. 5,719,399.

[51] Int. Cl.$^6$ .................................................... G01N 21/49
[52] U.S. Cl. ..................................... 250/341.8; 250/341.1
[58] Field of Search .............................. 250/341.8, 341.1, 250/358.1; 128/664

[56] References Cited

U.S. PATENT DOCUMENTS

| | | | |
|---|---|---|---|
| 4,945,239 | 7/1990 | Wist et al. | 250/358.1 |
| 5,180,122 | 1/1993 | Christian et al. . | |
| 5,296,853 | 3/1994 | Federow et al. . | |
| 5,371,368 | 12/1994 | Alfano et al. | 250/358.1 |
| 5,400,144 | 3/1995 | Gagnon . | |
| 5,475,370 | 12/1995 | Stern . | |
| 5,484,121 | 1/1996 | Padawer et al. . | |
| 5,500,530 | 3/1996 | Gregoris . | |

OTHER PUBLICATIONS

Patterson et al., "Absorption spectroscopy in tissue-simulating materials: a theoretical and experimental study of photon paths," Applied Optics, 34(1):22–30 (Jan. 1, 1995).

Tsuchiya et al., "Photon Migration Model for Turbid Biological Medium Having Various Shapes," Jpn. J. Appl. Phys., 34:L79–81 (Jan. 1, 1995).

Demos et al., "Temporal gating in highly scattering media by the degree of optical polarization," Opt. Lett., 21(2):161–3 (Jan. 15, 1996).

Demos et al., "Time resolved degree of polarization for human breast tissue," Optics Communications, 124:439–42 (Mar. 15, 1996).

Primary Examiner—Michael J. Tokar
Assistant Examiner—Richard Hanig
Attorney, Agent, or Firm—Kriegsman & Kriegsman

[57] ABSTRACT

A method and apparatus for imaging objects based upon the polarization or depolarization of light. According to one embodiment, there is provided a method for imaging the surface of a turbid medium, the method comprising the steps of: (a) illuminating the surface of the turbid medium with light, whereby light is backscattered from the illuminated surface of the turbid medium; (b) detecting a pair of complementary polarization components of the backscattered light; and (c) forming an image of the illuminated surface using the pair of complementary polarization components. Preferably, the illuminating light is polarized (e.g., linearly polarized, circularly polarized, elliptically polarized). Where, for example, the illuminating light is linearly polarized, the pair of complementary polarization components are preferably the parallel and perpendicular components to the polarized illuminating light, and the image may be formed by subtracting the perpendicular component from the parallel component, by taking a ratio of the parallel and perpendicular components or by using some combination of a ratio and difference of the parallel and perpendicular components.

11 Claims, 12 Drawing Sheets

IMAGING OF OBJECTS BASED UPON THE POLARIZATION OR DEPOLARIZATION OF LIGHT

CROSS-REFERENCE TO RELATED APPLICATIONS

The present application is a continuation-in-part of presently U.S. patent application Ser. No. 08/573,939, filed Dec. 18, 1995 now U.S. Pat. No. 5,719,399, which is herein incorporated by reference.

BACKGROUND OF THE INVENTION

The present invention relates generally to techniques for imaging objects located in or behind turbid media and more particularly to a novel technique for imaging objects located in, at the surface of or behind turbid media and, additionally, to a novel technique for detecting ice, snow and the like on airplane wings and similar surfaces.

As can readily be appreciated, there are many situations in which the detection of an object present in a turbid, i.e., highly scattering, medium is highly desirable. For instance, the detection of a tumor embedded within a tissue is one such example. One common technique for detecting tumors in tissues uses X;ray radiation. Although X-ray techniques do provide some measure of success in detecting objects located in turbid media, they are not typically well-suited for detecting very small objects, e.g., tumors less than 1 mm in size embedded in tissues, or for detecting objects in thick media. In addition, X-ray radiation can present safety hazards to a person exposed thereto. Ultrasound and magnetic resonance imaging (MRI) offer alternatives to the use of X-rays but have their own drawbacks.

Another technique used to detect objects in turbid media, such as tumors in tissues, is transillumination. In transillumination, visible light is incident on one side of a medium and the light emergent from the opposite side of the medium is used to form an image. Objects embedded in the medium typically absorb the incident light and appear in the image as shadows. Unfortunately, the usefulness of transillumination as a detection technique is severely limited in those instances in which the medium is thick or the object is very small. This is because light scattering within the medium contributes to noise and reduces the intensity of the unscattered light used to form the image shadow.

To improve the detectability of small objects located in a turbid medium using transillumination, many investigators have attempted to selectively use only certain components of the transilluminating light signal. This may be done by exploiting the properties of photon migration through a scattering medium. Photons migrating through a turbid medium have traditionally been categorized into three major signal components: (1) the ballistic (coherent) photons which arrive first by traveling over the shortest, most direct path; (2) the snake (quasicoherent) photons which arrive within the first δt after the ballistic photons and which deviate, only to a very slight extent, off a straight-line propagation path; and (3) the diffusive (incoherent) photons which experience comparatively more scattering than do ballistic and snake photons and, therefore, deviate more considerably from the straight-line propagation path followed by ballistic and snake photons.

Because it has been believed that ballistic and snake photons contain the least distorted image information and that diffusive photons lose most of the image information, efforts to make transillumination work most effectively with turbid media have focused on techniques which permit the selective detection of ballistic and snake photons while rejecting diffusive photons. This process of selection and rejection has been implemented in various time-gating, space-gating and time/space-gating techniques. Patents, patent applications and publications which disclose certain of these techniques include U.S. Pat. No. 5,140,463, inventors Yoo et al., which issued Aug. 18, 1992; U.S. Pat. No. 5,143,372, inventors Alfano et al., which issued Aug. 25, 1992; U.S. Pat. No. 5,227,912, inventors Ho et al., which issued Jul. 13, 1993; presently-pending and allowed U.S. patent application Ser. No. 07/920,193, inventors Alfano et al., filed Jul. 23, 1992; Alfano et al., "Photons for prompt tumor detection," *Physics World*, pp. 37–40 (January 1992); Wang et al., "Ballistic 2-D Imaging Through Scattering Walls Using an Ultrafast Optical Kerr Gate," *Science*, Vol. 253, pp. 769–771 (Aug. 16, 1991); Wang et al., "Kerr-Fourier imaging of hidden objects in thick turbid media," *Optics Letters*, Vol. 18, No. 3, pp. 241–243 (Feb. 1, 1993); Yoo et al., "Time-resolved coherent and incoherent components of forward light scattering in random media," *Optics Letters*, Vol. 15, No. 6, pp. 320–322 (Mar. 15, 1990); Chen et al., "Two-dimensional imaging through diffusing media using 150-fs gated electronic holography techniques," *Optics Letters*, Vol. 16, No. 7, pp. 487–489 (Apr. 1, 1991); Duncan et al., "Time-gated imaging through scattering media using stimulated Raman amplification," *Optics Letters*, Vol. 16, No. 23, pp. 1868–1870 (Dec. 1, 1991), all of which are incorporated herein by reference.

Of the above-listed art, Wang et al., "Kerr-Fourier imaging of hidden objects in thick turbid media," *Optics Letters*, Vol. 18, No. 3, pp. 241–243 (Feb. 1, 1993) is illustrative. In this article, there is disclosed a time/space-gating system for use in imaging opaque test bars hidden inside a 5.5 cm-thick 2.5% Intralipid solution. The disclosed system includes three main parts: a laser source, an optical Kerr gate and a detector. The laser source is a picosecond mode-locked laser system, which emits a 1054 nm, 8 ps laser pulse train as the illumination source. The second harmonic of the pulse train, which is generated by transmission through a potassium dihydrate phosphate (KDP) crystal, is used as the gating source. The illumination source is sent through a variable time-delay and is then used to transilluminate, from one side, the turbid medium containing the opaque object. The signal from the turbid medium located at the front focal plane of a lens is collected and transformed to a Kerr cell located at its back focal plane (i.e., the Fourier-transform spectral plane of a 4F system). That portion of the Kerr cell located at the focal point of the 4F system is gated at the appropriate time using the gating source to preferentially pass the ballistic and snake components. The spatial-filtered and temporal-segmented signal is then imaged by a second lens onto a CCD camera.

Although time- and/or space-gating techniques of the type described above have provided a modicum of success in improving transilluminated images, there still remains considerable room for improvement.

It has long been known that the accumulation of ice and/or snow on any lifting or control surface of an aircraft, such as an airplane wing or on a helicopter rotor, can lead to disastrous results. Accordingly, considerable effort has been expended in the past to devise techniques that enable the detection of ice and/or snow on airplane wings and similar surfaces. At present, a variety of ice detection techniques exist which have had varying degrees of success. Some such techniques rely on the thermal detection of ice, others on the electrical or ultrasonic detection of ice. Still other techniques, such as those disclosed in U.S. Pat. No. 5,500, 530, inventor Gregoris, which issued Mar. 19, 1996, U.S. Pat. No. 5,484,121, inventors Padawer et al., which issued Jan. 16, 1996, U.S. Pat. No. 5,400,144, inventor Gagnon, which issued Mar. 21, 1995, U.S. Pat. No. 5,296,853, inventors Federow et al., which issued Mar. 22, 1994, and U.S. Pat. No. 5,180,122, inventors Christian et al., which issued Jan. 19, 1993, all of which are incorporated herein by reference, rely on optical or electro-optical detection techinques.

In U.S. Pat. No. 5,475,370, inventor Stern, which issued Dec. 12, 1995, and which is herein incorporated by reference, there is disclosed a system for detecting the presence of an energy polarization altering dielectric material, such as ice or snow, on a surface, such as part of an aircraft, which normally specularly reflects incident energy, such as light, when there is no such dielectric present. The energy is conveyed from a transmitter along a path to the surface and the incident energy is reflected from the surface along a path to a receiver with a dielectric on the surface destroying any polarization, such as circular, of the energy and that reflected from a specular portion maintaining the polarization. An optical system in one or both of the paths operates in an isolator state to produce an image of the dielectric portion having a first intensity level and that of the specular portion passing through the optical system having a different intensity level. When the optical system is operated alternately in isolator and non-isolator states it produces an image of the dielectric portion having a relatively steady intensity level and that of the specular portion alternating between first and second different intensity levels corresponding to the isolator and non-isolator states of the optical system.

One problem noted by the present inventors with the technique of the above-identified Stern patent is that, because the Stern technique is based on the depolarization of specularly reflected light (with ice being treated as a dielectric material that destroys any polarization while metal maintains polarization), appropriate alignment of the plane of reflection of the object must be maintained with respect to the position of the illuminating source and the detector so that the specularly reflected light from the object is directed to the detector.

SUMMARY OF THE INVENTION

The present invention is based, in part, on the discovery that, when a pulse of initially-polarized light is used to illuminate a turbid medium, such as a human tissue, ice or snow, the ballistic and snake-like components of the light, which are either backscattered relatively directly from the surface of the turbid media or take direct paths through the turbid media, substantially maintain the polarization of the initially polarized light while the diffuse component of the light, which tends to travel longer, less direct paths through the turbid media before either being backscattered from the turbid media or emerging from the opposite end of the turbid medium, becomes compartively more depolarized than do the ballistic and snake-like components. Moreover, even where the pulse of light is initially unpolarized, the above discovery can be made use of since, when a pulse of initially unpolarized light is used to illuminate a turbid medium, such as a human tissue, the initially unpolarized light becomes partially polarized.

Therefore, according to one aspect, the present invention relates to a method for imaging the surface of a turbid medium, said method comprising the steps of: (a) illuminating the surface of the turbid medium with a pulse of light, whereby light is backscattered from the illuminated surface of the turbid medium; (b) detecting a pair of complementary polarization components of the backscattered light; and (c) forming an image of the illuminated surface using the pair of complementary polarization components.

According to another aspect, the present invention relates to a method for imaging an object located in or behind a turbid medium, said method comprising the steps of: (a) illuminating an object in or behind a turbid medium with a pulse of light, whereby light is backscattered from the object in or behind the turbid medium; (b) detecting a pair of complementary polarization components of the backscattered light; and (c) forming an image of the object using the pair of complementary polarization components.

Preferably, the pulse of illuminating light is polarized (e.g., linearly polarized, circularly polarized, elliptically polarized). Where, for example, the pulse of illuminating light is linearly polarized, the pair of complementary polarization components are preferably the parallel and perpendicular components to the polarized illuminating light, and the image may be formed by subtracting the perpendicular component from the parallel component, by taking a ratio of the parallel and perpendicular components or by using some combination of a ratio and difference of the parallel and perpendicular components.

The present invention is also based, in part, on the discovery that one can image a turbid medium at various depths thereof by illuminating the turbid medium with light pulses of different wavelengths and using a difference, ratio or some combination thereof of the respective perpendicular components to form an image.

Consequently, according to yet another aspect, the present invention relates to a method for imaging a turbid medium at a depth below the surface thereof, said method comprising the steps of: (a) illuminating the turbid medium with a first pulse of light of a first wavelength, the first pulse of light being polarized and having a first state of polarization, whereby said first pulse of light, after entering the turbid medium, emerges therefrom partially depolarized; (b) detecting a component of the partially depolarized first pulse of light that is normal to said first state of polarization; (c) illuminating the turbid medium with a second pulse of light of a second wavelength, said second wavelength being different from said first wavelength, the second pulse of light being polarized and having a second state of polarization, whereby said second pulse of light, after entering the turbid medium, emerges therefrom partially depolarized; (d) detecting a component of the partially depolarized second pulse of light that is normal to said second state of polarization; and (e) forming an image of the turbid medium using the normal components of the partially depolarized first and second pulses of light.

The first and second polarized pulses of illuminating light may be, for example, linearly polarized light, and the image may be formed by subtracting the perpendicular component obtained from one pulse from the perpendicular component obtained from the other pulse, by taking a ratio of the respective perpendicular components or by using some combination of a ratio and difference of the respective perpendicular components.

The present invention is also based, in part, on the discovery that different types of materials, such as diffusively reflective metals on one hand and ice and/or snow on the other hand, depolarize polarized light to different extents and that, therefore, the presence of ice and/or snow on airplane wing or a similar structure can be detected by observing the extent to which polarized light used to illuminate an airplane wing or the like becomes depolarized. Moreover, even where the pulse of light is initially unpolarized, the above discovery can be made use of since, when a pulse of initially unpolarized light is backscattered off the surface of a metal or dielectric, the two polarization components of the backscattered light differ in intensity.

Consequently, according to yet another aspect, the present invention relates to a method for detecting snow or ice on an airplane wing or the like, said method comprising the steps of: (a) illuminating an airplane wing with a pulse of light, whereby light is diffusively backscattered from the illuminated airplane wing; (b) detecting a pair of complementary polarization components of the diffusively backscattered light; and (c) using the pair of complementary polarization components to determine whether snow or ice is present on the illuminated airplane wing.

The technique of the present invention is, therefore, to be contrasted with the above-discussed Stern technique in that, in the present technique, ice and metal are treated as light scattering objects and diffusively reflected light, as opposed to specularly reflected light, is used. In fact, the present inventors have found the use of specularly reflected light in the Stern technique to be troublesome in that it often creates "hot areas" in images.

The present invention is also directed to apparatuses for performing the above-described methods.

Additional objects, features, aspects and advantages of the present invention will be set forth in part in the description which follows, and in part will be obvious from the description or may be learned by practice of the invention. Various embodiments of the invention will be described in sufficient detail to enable those skilled in the art to practice the invention, and it is to be understood that other embodiments may be utilized and that changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts.

DETAILED DESCRIPTION OF PREFERRED EMBODIMENTS

The present invention relates to a method that enables high resolution and high-speed optical imaging of objects located in, at the surface of, or behind highly scattering media using polarized illuminating light and polarization-difference imaging. Using the present invention, surface, as well as beneath-the-surface, imaging of tissues and other turbid media can be achieved in a backscattered geometry. The surface image information is predominately carried by the parallel polarization image component while the perpendicular image component contains beneath-the-surface image information. Images of structures at different depths within a turbid medium can be obtained using the perpendicular polarization component resulting from the use of different illuminating wavelengths.

The present invention also relates to a method that enables improved optical image quality and visibility of object features based on the principle that, when an object is illuminated with polarized light, the parallel component of light scattered by the object is more intense than the perpendicular component thereof. Using this principle, ice on the wings of a plane or mines in the sea can be detected by illuminating with polarized light, detecting the resultant parallel and perpendicular polarization components, and subtracting the perpendicular polarization component from the parallel polarization component, any changes in depolarization likely being caused by the presence of ice on the wing or a mine in water. In addition, the images of objects in smoke, fog or smog can be made more visible by obtaining the parallel and perpendicular components in the manner discussed above and subtracting the perpendicular component from the parallel component so as to cancel-out the effects of the diffusive photons responsible for obscuring the image.

Figure 1:
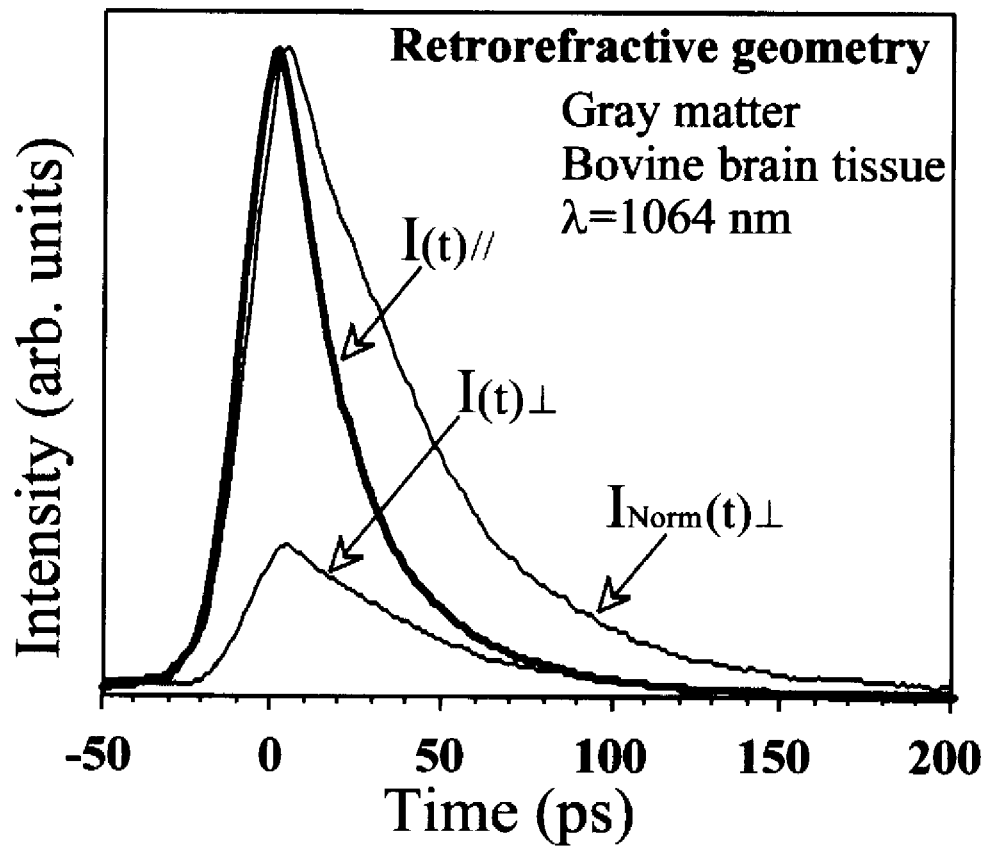
FIG. 1 is a graphic representation of temporal profiles of the parallel polarization component, perpendicular polarization component and normalized perpendicular polarization component of backscattered light obtained from bovine gray matter brain tissue illuminated with 1064 nm, 6.5 ps laser pulses.

Referring now to FIG. 1, there is shown a graphic representation of the parallel ($I_{(t)\|}$), perpendicular ($I_{(t)\perp}$), and normalized perpendicular ($I_{(t)\perp}$) components of backscattered light detected from a sample of bovine gray matter brain tissue using the following experimental setup: The laser system used was a synchronously-pumped tunable R-6G dye laser pumped by a mode-locked, pulse-compressed Nd:YAG laser. The 6.5 ps, 1064 nm laser pulses and a streak camera with a fiber probe were used to record the temporal profiles of the backscattered light. For the imaging measurements, the dye laser beam tunable in the 570–635 nm spectral region was used as the illuminating source with average power of about 5 mW. A cooled CCD camera and imaging optics were used to record the parallel and perpendicular image components with exposure time of 200 msec.

FIG. 1 shows the polarization components of the backscattered light when linearly polarized 1064 nm pulses were used. The diameter of the illuminating beam was 0.5 mm. As can be seen in FIG. 1, the parallel polarization component ($I_{(t)\|}$) is more intense than the perpendicular polarization component ($I_{(t)\perp}$). In addition, when the temporal profile of the perpendicular component was normalized to the peak intensity of the parallel component ($I_{norm(t)\perp}$), the temporal profiles were different, having different peak time positions and four wave harmonic mixing (FWHM). The scattering parameters of gray matter allow for clear observation of the above mentioned differences in the two backscattering polarization components within the temporal resolution of our system (about 15 ps). Similar differences are present in different types of tissue but with different time profiles and peak intensities.

Without wishing to be limited to any theory, it is believed that the reason for the differences in the two polarization components arises from the fact that the backscattered photons that are perpendicularly polarized must first undergo sufficient scattering events to lose their polarization information. By contrast, the photons that are directly backscattered from the surface of the tissue have less of an opportunity to depolarize; therefore, the backscattering photons from the surface of the tissue and initial layers beneath the surface belong mostly to the parallel polarization image component. However, the perpendicular polarization component contains predominately photons that penetrated the tissue to certain depths before they emerged in the backscattering direction. This salient concept explains the differences in the temporal profiles of the two polarization components shown in FIG. 1. The parallel component contains all photons backscattered from the surface of the tissue before they depolarize. As a result, the parallel component is more intense and the time of peak intensity is when the backscattered light from the surface arrives. The perpendicular component time of peak intensity arises from the depolarized photons that propagated the tissue to a certain depth and then backscattered.

Figure 2:
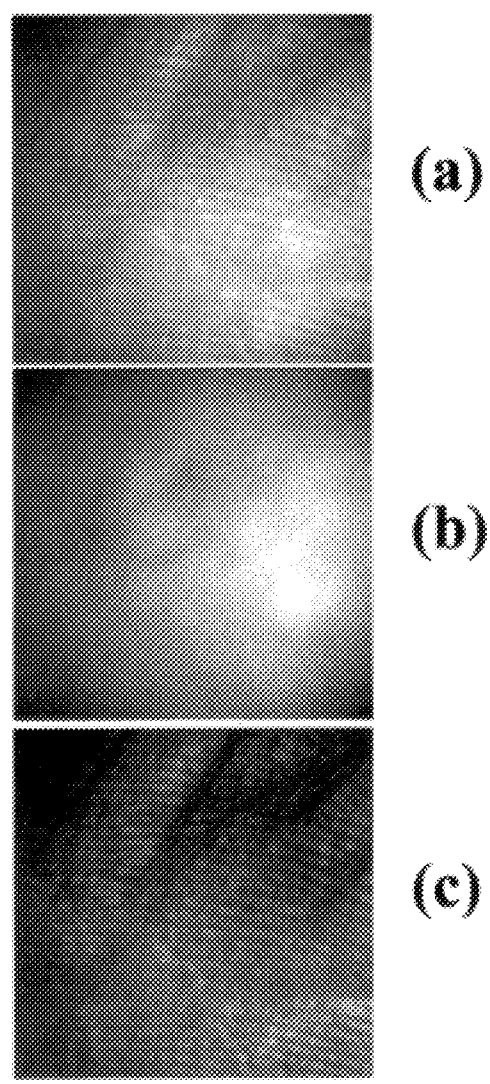
FIGS. 2(a) through 2(c) are images of a human palm illuminated with 580 nm polarized laser pulses and obtained using (a) the parallel polarization image component; (b) the perpendicular polarization image component; and (c) the parallel polarization image component minus the perpendicular polarization image component, respectively, of the backscattered light.

The above results suggest that image information of the surface and near-surface of tissues is contained predominately in the parallel polarization image component while the perpendicular polarization component contains information of that portion of the tissue well beneath the surface. This concept is demonstrated in FIGS. 2(a) through 2(c) where a 580 nm linearly polarized laser beam was used to illuminate the palm of a human hand and a CCD detector was used to record the two polarization image components (i.e., parallel and perpendicular). FIG. 2(a), which is the parallel polarization image, shows detailed structures of the skin. FIG. 2(b), which is the perpendicular polarization image, shows no skin structures. The gray shades in FIG. 2(b) are due to the differing blood concentrations under the skin. The parallel image component contains photons backscattered from the skin and after penetrated underneath the skin while the perpendicular image predominately contains photons that have penetrated underneath the skin. Consequently, subtracting the two image polarization components, a clearer image of the skin can be obtained. This is demonstrated in FIG. 2(c), where the image is obtained by direct subtraction of the two polarization components (FIGS. 2(a) and 2(b)). The image component arising from photons that propagated deep enough into the tissue and lost their polarization information is equally split between the two image polarization components. By subtracting the two image polarization components, the depolarized image component arising from the photons that propagated through the skin before retroreflected should cancel out. The image obtained is formed by photons that are still polarized because they have undergone less scattering; consequently, they predominately belong to the photons backreflected from the surface or slightly beneath the surface. This process leads to an image which contains detailed information about the surface of the skin structures, as demonstrated in FIG. 2(c).

The time profile of the backscattered pulse is given by the following relation:

$$J(\mu'_s, \mu_a, t) = I_0 S(\mu'_s, t) \exp(-\mu_a c t)$$

where $\mu'_s$ is the transport scattering coefficient, $\mu_a$ is the absorption coefficient, $I_0$ is the intensity of the injected pulse while $S(\mu'_s, t)$ and $\exp(-\mu_a c t)$ represent scattering and absorption, respectively. The temporal profile of the retroreflected pulse strongly depends on $\mu_a$. For larger $\mu_a$, the FWHM of the backscattered pulse is smaller, indicating a shorter average distance of flight <L> of the recorded photons. The mean photon-visit depth $\bar{z}$ of the backscattered photons depends on $\mu_a$, as well as $\mu'_s$, while in a time resolved measurement, the dependence of $\bar{z}(t)$ is nearly linear to the square root of the detection time. This means that using different illuminating wavelengths, the decay time of the temporal profile of the backscattered light pulse and, consequently, $\bar{z}$ can be appropriately adjusted by changing $\mu'_s$ and $\mu_a$. In addition, FIGS. 1 and 2(a) through 2(c) demonstrate that the perpendicular polarization component contains photons that propagated inside the tissue before being backscattered and are almost free from scattering from the surface.

Based on the above concepts, it can be appreciated that structures located at different depths inside a tissue can be imaged using the following principles: (a) different illuminating wavelengths can be used to reach different mean photon-visit depths $\bar{z}(t)$; (b) the perpendicular polarization image component can be used to avoid the image information from the surface of the tissue; (c) the intensity and time of exposure can be adjusted so that using the same parameters in pulsed illumination one can have equal peak intensities of the temporal profiles of the backscattered pulses for the different wavelengths; and (d) images obtained under different illuminating wavelengths can be subtracted to obtain a new image of structures underneath the surface. The images obtained in this way contain information from different depths $\bar{z}$ but, due to normalization, images from the front part of the tissue cancel out, and the remaining image arises from the photons that propagated deeper into the tissue in the longer wavelength image. Consequently, by selecting appropriate illuminating wavelengths, one can effectively reach different "depth zones" inside the tissue.

Figure 3:
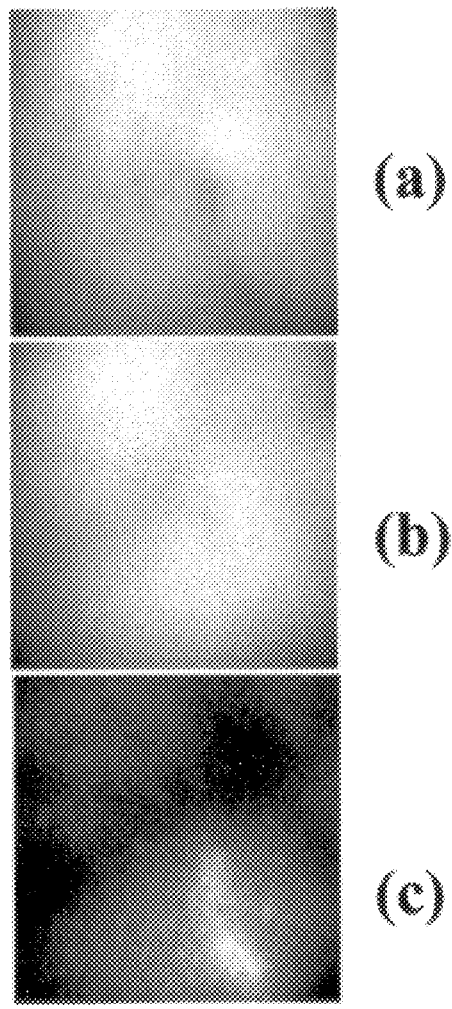
FIGS. 3(a) through 3(c) are images of the back of a human hand formed using (a) the perpendicular polarization component backscattered from the hand following 570 nm illumination; (b) the perpendicular polarization component backscattered from the hand following 600 nm illumination; and (c) the difference obtained by subtracting the perpendicular polarization component of (a) from (b)

Referring now to FIGS. 3($a$) through 3($c$), the results of the aforementioned technique can be seen. The image in FIG. 3($a$) shows the perpendicular image component under 570 nm illumination of the back of a hand. Due to high absorption by the hand tissue at this wavelength, the photons backscattered do not penetrate the tissue much and, as a result, only a scratch on the skin located in the lower right corner of FIG. 3($a$) can be seen as a dark line. FIG. 3($b$) shows the perpendicular polarization image under 600 nm illumination at the same position. The absorption of blood at 600 nm is about 10 less than at 570 nm, allowing for a deeper propagation of the 600 nm photons before being backscattered. The scratch at the lower right side cannot be seen due to the fact that it is superficial and its presence is masked by photons at 600 nm that have propagated deeper into the tissue. However, one can barely see in FIG. 3($b$) some veins located underneath the skin. Subtraction of the 570 nm image from the 600 nm image leads to an image arising from photons that propagate to deeper layers that were reached by the 600 photons but not by the 570 nm photons. This principle is demonstrated in FIG. 3($c$), where the veins under the skin are clearly observable as darker structures with actual size about 1 mm while the scratch is shown in the lower right corner as a structure of brighter intensity. The exposure time/illuminating intensity for the two images was appropriately adjusted so that the image components from the outer part of the tissue were cancelled-out during image subtraction. The exposure parameters were obtained using the method described above so that the peak intensities of the time profiles under 570 and 600 nm pulsed illumination were equal.

Figure 4:
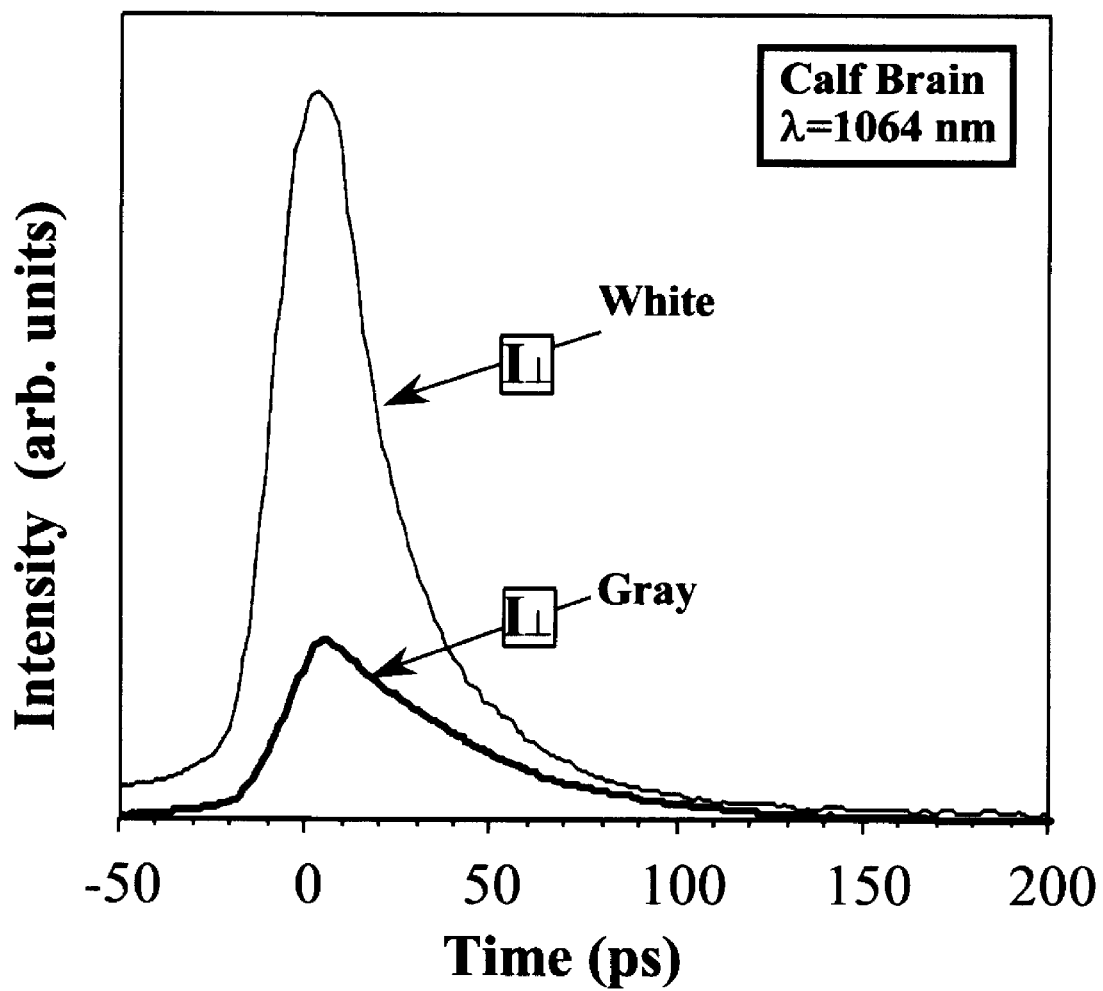
FIG. 4 is a graphic representation of the respective perpendicular polarization components backscattered from bovine gray and white matter following 1064 nm, 6.5 ps illumination.

The aforementioned imaging technique of image polarization subtraction at different wavelengths can be used to highlight differences in absorption by blood or scattering due to the presence of different types of tissues at different depths using differences in $\mu_a$ and $\mu'_s$. Referring now to FIG. 4, there is shown the backscattered perpendicular polarization components of bovine gray and white matter, respectively, using 1064 nm, 6.5 ps pulsed illumination. The perpendicular polarization component of white matter is more intense than that of the gray matter because of higher scattering and depolarization. The difference in scattering and depolarization from different types of tissues enables different structures inside the tissue to be observed using the polarization difference technique of the present invention. With gradual changes of the illuminating wavelengths (and adopting appropriate optical techniques, such as confocal microscopy), one may be able to display histological structures at different depths. The maximum depth at which imaging may be achieved will depend on the scattering and absorption characteristics of the particular tissues involved.

Therefore, it can be appreciated that optical polarization imaging of the type herein described can be used to obtain images at surfaces and at different depths. The surface of a tissue can be highlighted and imaged better by subtraction of the two image polarization components at the same illuminating wavelength. Images underneath the skin can be obtained by subtraction of the perpendicular polarization components at different illuminating wavelengths. This technique can be used for in vivo imaging of the skin, mucosa, vascular and arterial systems, GYN and gastrointestinal track, with relatively simple equipment and high speed of image formation that will allow imaging in real time.

When polarized light is scattered by an object (i.e., diffuse reflection), the two polarization components (parallel and perpendicular to the initial polarization state) of the scattered light are not equal in intensity due to differences in scattering and reflection by the object. The backscattered light can be separated into two segments, the still polarized segment and the depolarized segment. The still polarized segment belongs to the parallel polarization component of the backscattered light while the depolarized segment is evenly distributed between the two polarization components. As a result, the parallel polarization component of the backscattered light is more intense than the perpendicular. The degree that light depolarizes when scattered by an object depends on the optical properties of the object. For example, scattering by a metallic object depolarizes light very little whereas scattering by an object which light is capable of penetrating and being multiply scattered internally before exiting the medium (e.g., biological systems, ice, snow, etc.) depolarizes light much more.

Figure 5A:
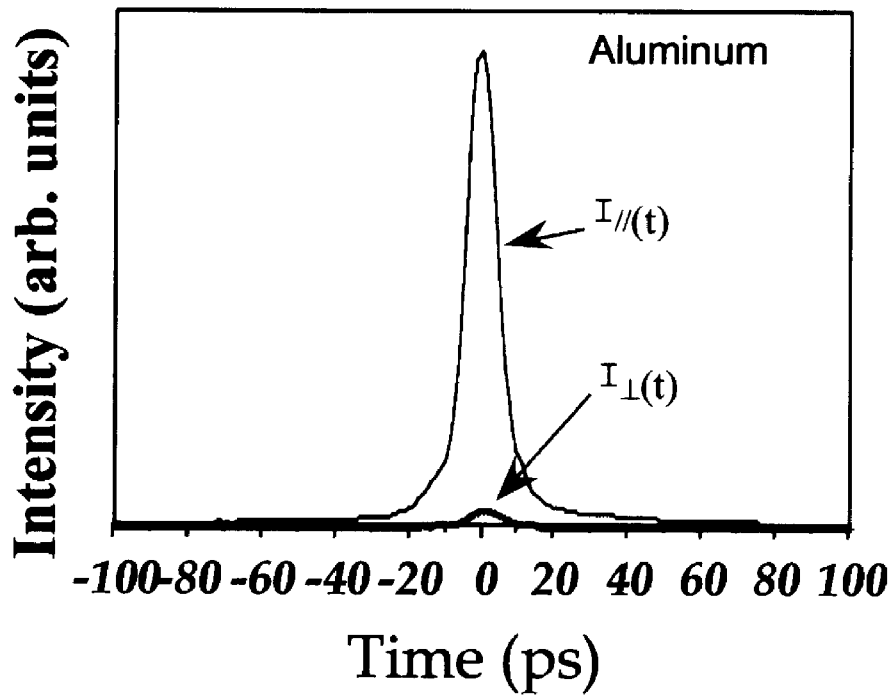
FIGS. 5(a) and 5(b) are graphic representations of the parallel and perpendicular polarization components detected from backscattered light following 532 nm, 4 ps laser pulse illumination of (a) an aluminum plate and (b) 1 mm ice deposited on the aluminum plate, respectively.
Figure 5B:
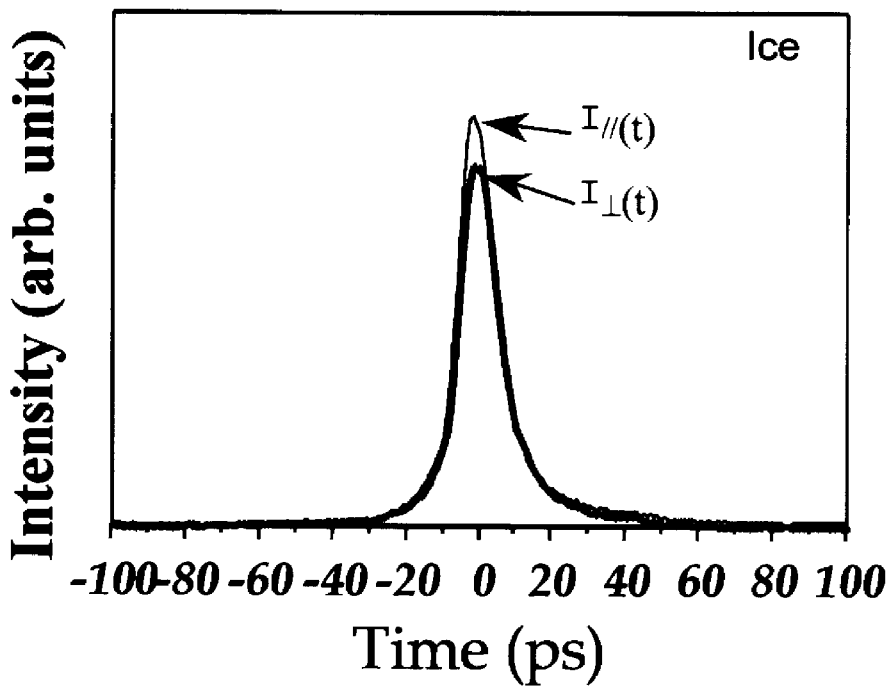
Figure 6A:
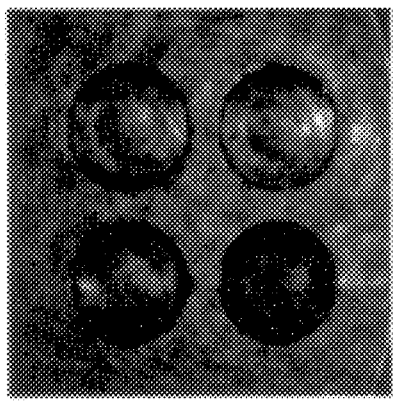
FIGS. 6(a) through 6(e) are images of a square copper plate where four 1.25 cm diameter holes of different depths (0.25 mm, 0.5 mm, 1 mm and 2 mm) are filled with ice, the plate being illuminated with linearly polarized laser light at 632.8 nm, a cooled CCD camera being used to record the image, and (a) no polarizer being positioned in front of the CCD camera, (b) a polarizer being positioned in front of the CCD, the polarizer being oriented parallel to the polarization of the illuminating light, (c) a polarizer being positioned in front of the CCD, the polarizer being oriented perpendicular to the polarization of the illuminating light, (d) the image being obtained from the difference between the parallel and perpendicular components ($I_\parallel - I_\perp$), and (e) the image being obtained from the difference between the parallel and perpendicular components divided by the perpendicular image [$(I_\parallel - I_\perp)/I_\perp$]
Figure 6B:
Figure 6C:
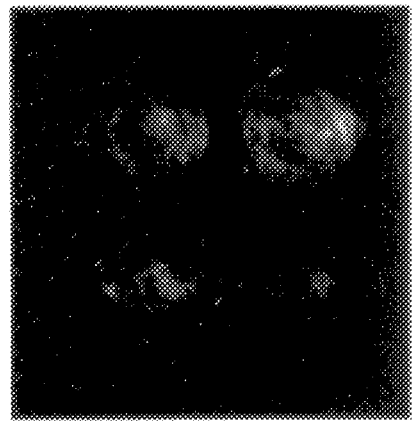
Figure 6D:
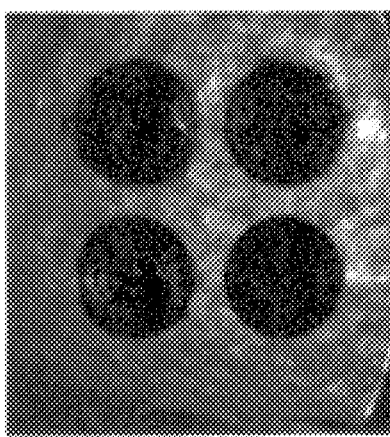
Figure 6E:
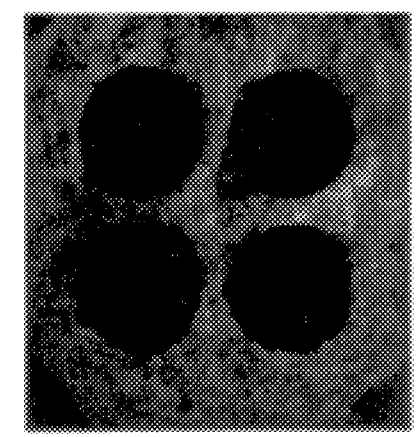

A pulse-compressed Nd:YAG laser emitting 532 nm, 4 ps pulses was used to illuminate an aluminum plate and ice deposited on the same aluminum plate. Backscattered light was collected using a fiber probe, and the temporal profile of the parallel and perpendicular polarization components were recorded by a streak camera with 10 ps time-resolution. The recorded time profiles of the two polarization components of the backscattered pulse for aluminum and ice are shown in FIGS. 5($a$) and 5($b$), respectively. As can be seen in FIG. 5($a$), the backscattered parallel polarization component for aluminum (airplane wing) is much more intense than the perpendicular polarization component. However, as can be seen in FIG. 5($b$), when ice 1 mm thick on the aluminum plate (to simulate ice on the wing of an airplane) was illuminated with polarized light, the difference in intensity between the two polarization components was significantly smaller and the relative intensity of the two backscattered polarization components was very different than for the bare aluminum plate.

Additional imaging and detection of ice on a metal surface is shown in FIGS. 6($a$) through 6($e$). In a square copper plate there are four 1.25 cm diameter holes of different depth (0.25, 0.5, 1 and 2 mm) which are filled with ice. The target is illuminated with linearly polarized laser light at 632.8 nm and a cooled CCD camera is used to record the image formed by the photons scattered off the ice or metal surface. The metal surface was slightly rotated so that no specularly reflected light reaches the CCD camera. Specularly reflected light is causing the formation of "hot spots" in the image which may inhibit the detection of ice or make it more difficult to detect. FIG. 6($a$) shows the image of the target with no polarizer in front of the CCD. The four circular holes filled with ice can be seen aligned at the corners of an inner square. FIG. 6($b$) shows the parallel polarization image of the target (polarizer in front of the CCD is parallel with the polarization of the illuminating light) while FIG. 6(c) shows the perpendicular image component. As discussed in the previous paragraph, the ice in the parallel image appears darker than the metal while in the perpendicular image, the ice appears brighter than the metal. FIG. 6(d) shows the image obtained after subtraction of the two image components while FIG. 6(e) represents the $(I_{parallel} - I_{perpendicular})/I_{perpendicular}$ image. In the resulting images shown in FIGS. 6(d) and 6(e), the ice is recorded with much less intensity than the metal (FIG. 6(e) provides the highest contrast) demonstrating the usefulness of this technique for ice detection and imaging.

Based on the above, a polarization-difference under polarized illumination imaging system is herein described that enables enhanced visibility of target-object features in a light-scattering environment or in a light-transparent environment. The designing principles of this system are as follows: (1) polarized light is used for the illumination of the target; (2) the two image polarization components are recorded; and (3) the perpendicular image component is subtracted from the parallel image component to obtain the final image of the object.

The first of the above requirements can be satisfied in some cases even if the primary light source is unpolarized. It is known that when unpolarized light is reflected off the surface of a metal or a dielectric, the two polarization components of the reflected light are different in intensity depending upon the wavelength and the angle of incidence of the illuminating light (Fresnel's laws of reflection). As a result, the light reflected off the metal or dielectric object becomes partially polarized. In other instances, optical anisotropy of an object causes an initially unpolarized light illuminating the object to become partially polarized when reflected off the object. In still other instances, when unpolarized light propagates through the interface of two dielectrics, it becomes partially polarized and, therefore, an object inside the second dielectric is illuminated with partially polarized light. The optical polarization difference method of the present invention can, therefore, be used in all of the above instances by recording the two polarization image components and calculating the difference between the two components (or performing some other interimage operation on the two components) to obtain the optical polarization difference (OPDI) image of the object even though the primary illuminating source was not polarized.

The optical polarization difference technique of the present invention can be used in a variety of applications where the scattering of light by the environment inhibits clear observation of the target-object or when target features need to be revealed. The present technique is hereinafter described in two contexts: (a) imaging when an object is surrounded by an intense scattering medium; and (b) detection of object features.

When polarized light travels through a scattering medium (such as fog, smog, smoke, etc.), a gradual process of depolarization takes place. The light completely loses its polarization only after traveling a long distance into the smoke or fog or smog. When partially polarized light illuminates the object, the two polarization components of the reflected light are different in intensity with the parallel component more intense than the perpendicular. Similarly, unpolarized light reflected off an object can give rise to different intensities for the two polarization components (defined by the plane of incidence of the light or the optical anisotropy axis of the material) as discussed above. As the partially polarized reflected light from the object travels through smoke or the like towards a detection system it continues to be depolarized. The light that reaches the detection system, therefore, has been depolarized greatly due to scattering in the smoke and due to scattering in the object. However, the still polarized photons are carrying the image information even though their relative intensity with respect to the diffusive-unpolarized photons decreases. As a result, the image quality decays and the image is lost in the "white" background made up of the unpolarized diffusive light. Subtraction of the two polarization image components cancels-out the depolarized component as well as the background light (which is unpolarized), and the generated polarization-difference image is made up of the still polarized photons that have undergone less scattering in the smoke and contain the image information. In this way, the "white" background from the diffusive photons is subtracted and the image is revealed again. The visibility inside the fog or smog or smoke is improved while the range at which the image is observable depends on the density of the smoke or fog or smog as well as on the detection system. In general, as long as there are polarized photons reaching the detector, an image of the object can be reconstructed using polarization difference imaging.

The technique of the present invention can be used to increase the observation depth of a fireman entering a building or space filled with smoke. Similarly, the present technique can be used to help a driver of a car or train or the pilot of a plane to see better and in greater depth in fog.

The present invention can also be used to detect ice on the wings of a plane in the following manner: Polarized light is used to illuminate a wing of a plane. The two polarization image components scattered by the wing are detected and the difference between them is calculated to obtain a polarization-difference image. The background light component cancelsout because it is evenly distributed in both polarization image components. The polarized light scattered by the ice-free portions of the aluminum wing remains almost completely polarized, as in FIG. 5(a). However, the light scattered by the ice-covered part of the wing is strongly depolarized, as in FIG. 5(b). As a result, the ice-covered part of the plane in the perpendicular image component is shown having a higher intensity than that for the ice-free part of the plane whereas the parallel image component is shown having a lower intensity than that for the ice-free part of the plane. Consequently, the polarization-difference image shows the ice-free part of the wing with high intensity because of the big difference in intensity between the parallel and perpendicular components scattered by the ice-free part of the wing, and the ice-covered part of the wing with low intensity because of the small difference in intensity between the parallel and perpendicular components scattered by the ice-covered part of the wing.

Based on the differences in depolarization that take place when polarized light is scattered by the wing of a plane when ice is or is not present thereon, a number of different techniques can be used to detect ice on a wing. For example, the detection of ice can be performed using a polarization-difference image of the type described above. Alternatively, the difference of the two polarization image components $(I\| - I\perp)$ can be replaced by any image operation containing $I\|$ and $I\perp$, such as $I\|/I\perp, [I\|-I\perp]/[I\|+I\perp], [I\perp]/[I\|-I\perp], [I\|-I\perp]/[I\perp]$ and $[I\|]/[I\|-I\perp]$.

Detection of ice can also be performed by scanning the wing of the plane with a polarized light beam and detecting point-by-point the depolarization of the scattered light. The intensities of the two polarization components of the initially polarized beam are simultaneously measured and the ratio of the parallel over the perpendicular intensities from each point on the wing (I∥/I⊥) is calculated. When the ratio is high [(I∥/I⊥)>>1], the wing is free of ice. When the ratio approaches 1 [1<(I∥/I⊥)<2], there is ice on the wing. In the point-by-point scanning technique, instead of using the ratio (I∥/I⊥), one may choose to use other functions, such as (I∥–I⊥), [I∥–I⊥]/[I∥+I⊥], [I⊥]/[I∥–I⊥], [I∥–I⊥]/[I⊥] and [I∥]/[I∥–I⊥].

The foregoing technique can be used in a variety of applications. For example, the detection of mines in the sea can be achieved using the above method. The scattering and depolarization of polarized light by a mine will provide the basis for detection of the mine. Sunlight may be used as the illuminating source, which will be partially polarized under the water depending upon its angle of incidence with respect to the sea. Subtraction of the two polarization image components will reveal the change in depolarization in the field of observation introduced by the mine and will pinpoint the location of the mine. The present technique can also be used to detect target features when the target exhibits optical anisotropy.

Figure 7:
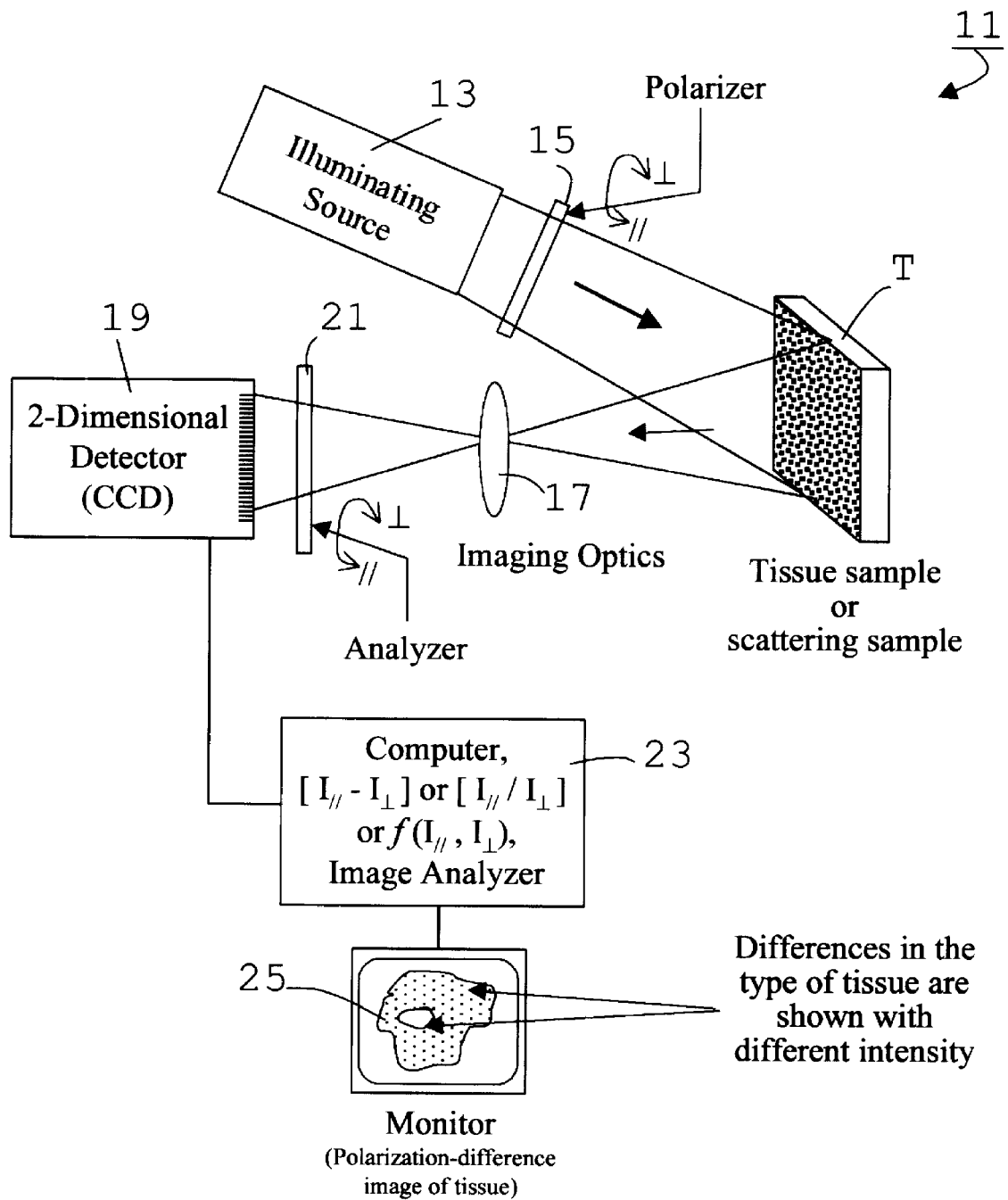
FIG. 7 is a schematic view of a first embodiment of an imaging system constructed according to the teachings of the present invention, the imaging system being shown used in a medical application.

Referring now to FIG. 7, there is shown a schematic view of a first embodiment of an imaging system constructed according to the teachings of the present invention, the imaging system being represented generally by reference numeral 11.

System 11, which may be used, as in FIG. 7, to image tissue samples T, comprises an illuminating light source 13. Light source 13 may be a laser, a lamp or the like. System 11 also includes a rotatably-mounted polarizer 15, which is used to ensure that the light from source 13 is polarized. System 11 further includes imaging optics 17 for imaging backscattered light from tissue sample T onto a 2-dimensional cooled CCD camera 19. A rotatably-mounted analyzer 21, which is used to select the parallel and perpendicular components of the backscattered light, is positioned between optics 17 and camera 19. As can readily be appreciated, to enable the detection of both the parallel and perpendicular components of the backscattered light, one may either keep polarizer 13 in the parallel position while sequentially placing analyzer 21 in the parallel and perpendicular positions or vice versa.

System 11 also includes 23 a computer for analyzing the information detected by detector 19 regarding the parallel and perpendicular components of the backscattered light in the manner discussed above and a monitor 25 for displaying an image of the illuminated tissue sample in accordance with the data outputted by computer 23.

Figure 8:
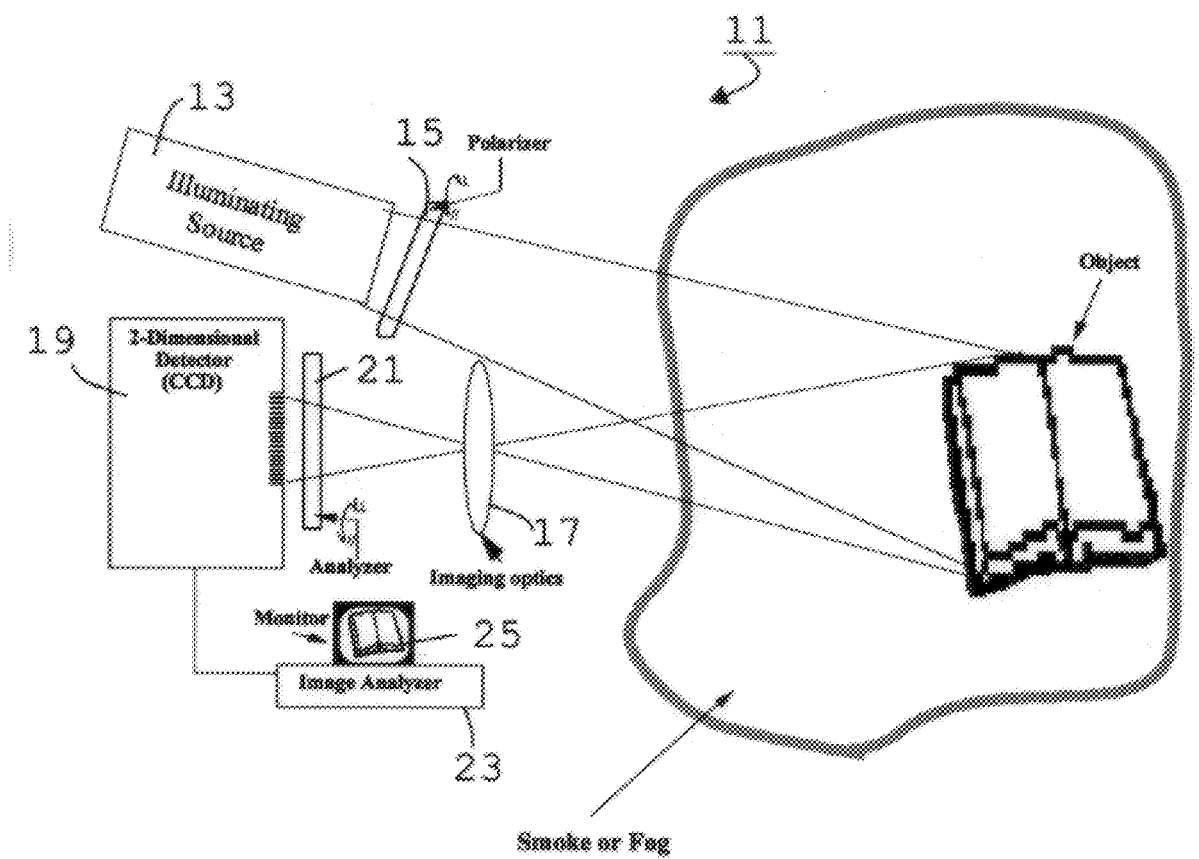
FIG. 8 is a schematic view of the imaging system of FIG. 7 being used in a non-medical application.

Referring to FIG. 8, system 11 can be seen being applied to non-medical imaging.

Figure 9:
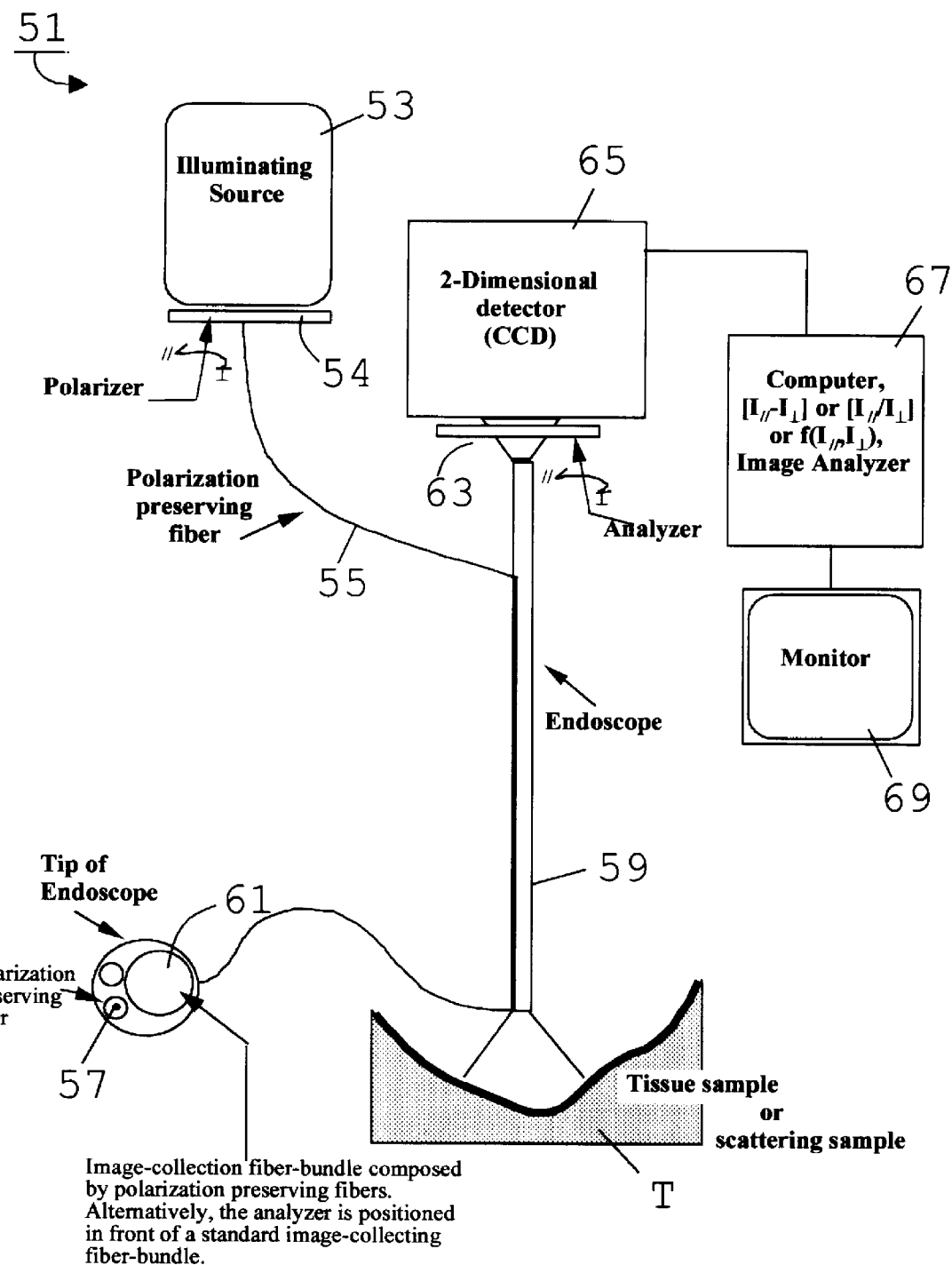
FIG. 9 is a schematic view of a second embodiment of an imaging system constructed according to the teachings of the present invention, the imaging system being adapted for either medical or non-medical applications.

Referring now to FIG. 9, there is shown a second embodiment of an imaging system constructed according to the teachings of the present invention, the imaging system being represented generally by reference numeral 51.

System 51 includes an illuminating source 53, which may be the same as illuminating source 13 of system 11. System 51 also includes a rotatably mounted polarizer 54, which is used to ensure that polarized light is inputted into a polarization preserving fiber 55. Fiber 55, in turn, is disposed within a working channel 57 of an endoscope 59 and may be used to illuminate a tissue sample T. The backscattered light from tissue sample T is collected by an image-collection fiber bundle 61 disposed within endoscope 59. A rotatably-mounted analyzer 63 is located at the distal end of bundle 61 and is used to select the parallel and perpendicular components of the backscattered light. (As can readily be appreciated, either polarizer 54 can be placed in the parallel position while analyzer 63 is placed in the parallel and perpendicular positions or vice versa.) The light passed through analyzer 63 is then detected by a detector 65, the output of which is then transmitted to a computer 67. A monitor 69 is coupled to computer 67 for displaying the image.

Figures 10A, 10B:
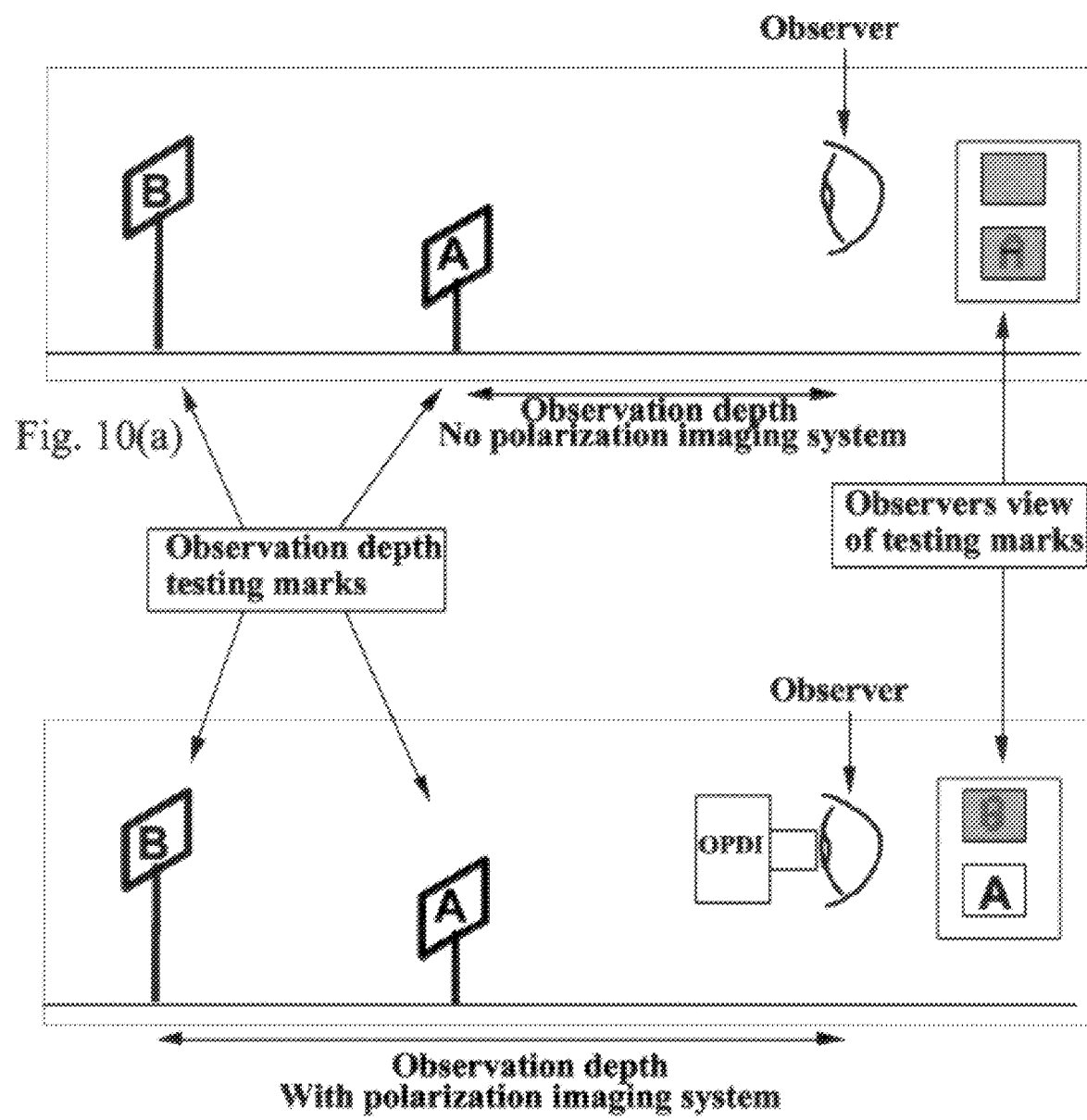
FIGS. 10(a) and 10(b) are schematic diagrams illustrating the improvement in observation depth in turbid media obtainable using the technique of the present invention.

Referring now to FIGS. 10(a) and 10(b), there is schematically shown the improvement in observation depth made possible using the technique of the present invention. As seen in FIG. 10(a) (where the technique of the present invention is not employed), the test mark (A) can barely be seen by the naked eye of an observer whereas, as seen in FIG. 10(b) (where the technique of the present invention is employed), the test mark (A) can be seen clearly, and observation depth increases to reach test mark (B).

Figure 11:
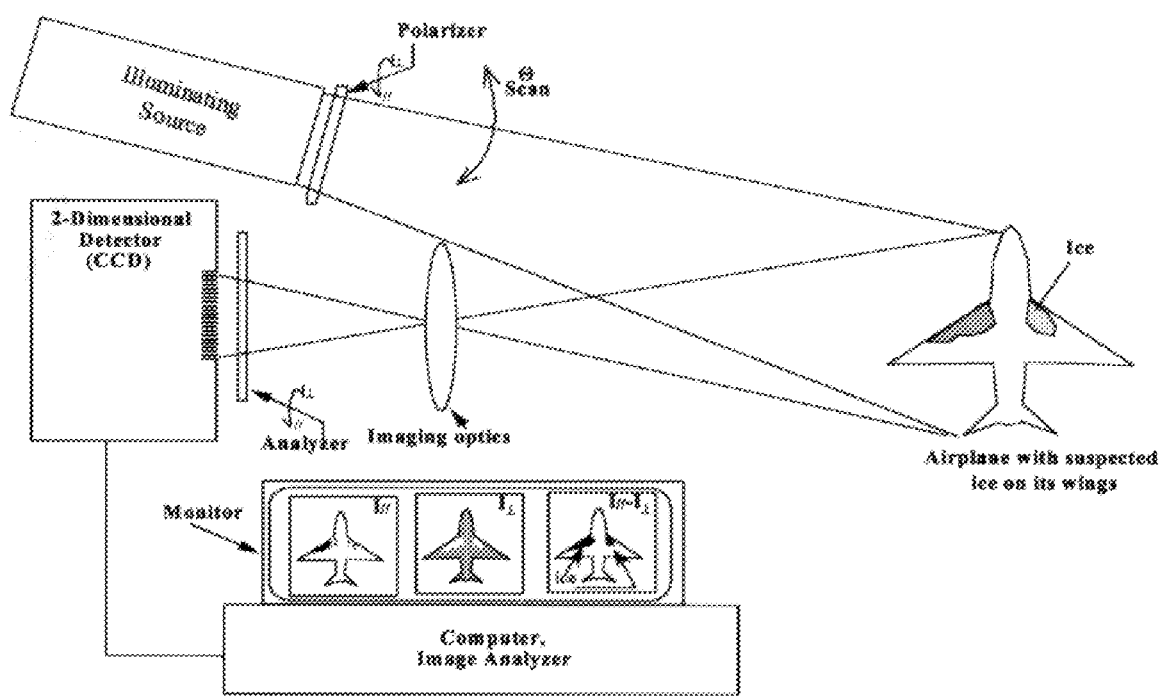
FIG. 11 is a schematic view of a third embodiment of an imaging system constructed according to the teachings of the present invention, the imaging system being particularly well-adapted for detecting ice on airplanes.
Figure 12:
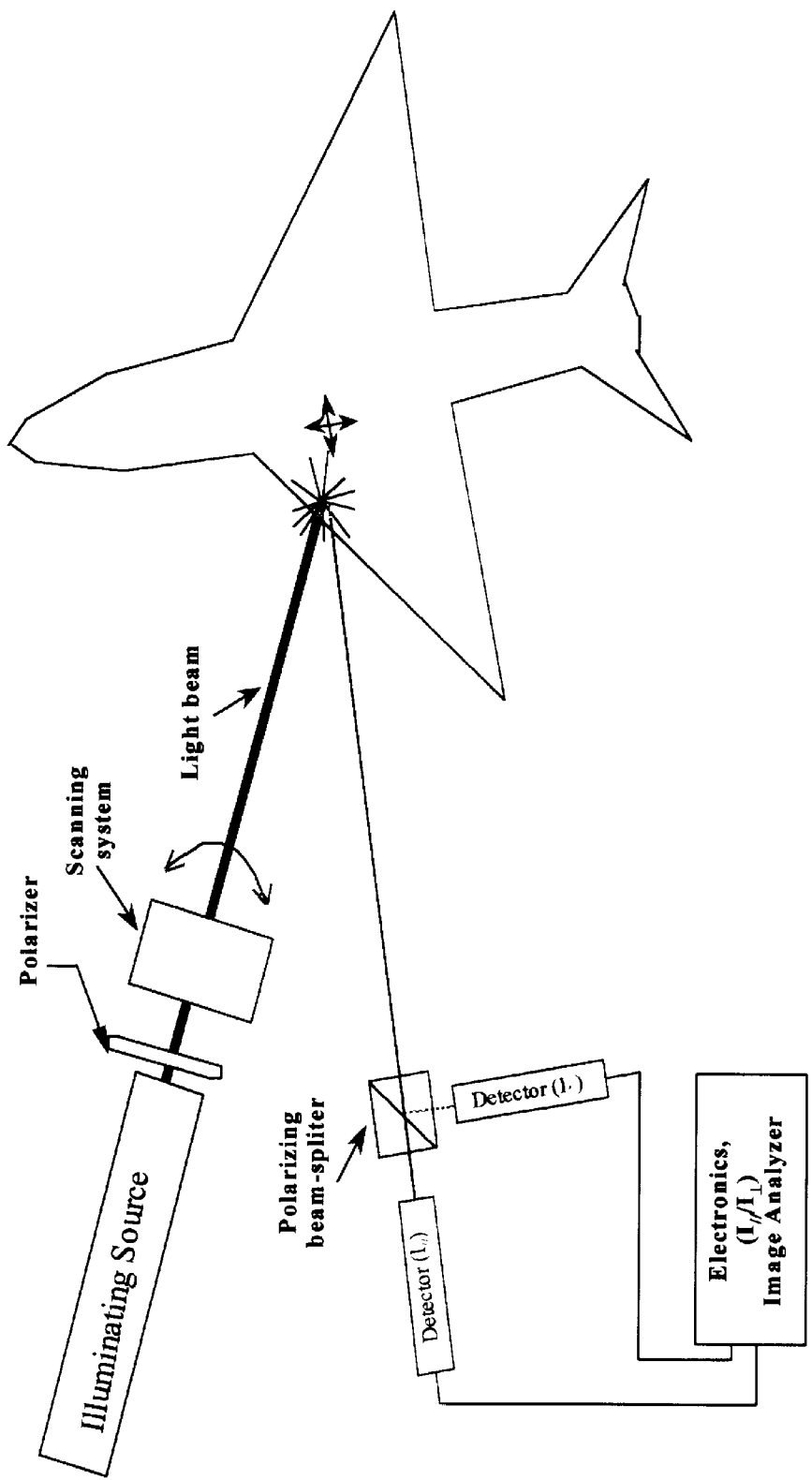
FIG. 12 is a schematic view of a fourth embodiment of an imaging system constructed according to the teachings of the present invention, the imaging system being particularly well-adapted for detecting ice on airplanes.

Referring now to FIGS. 11 and 12, there are shown schematic views of a third and a fourth embodiment of an imaging system constructed according to the teachings of the present invention, the imaging systems of FIGS. 11 and 12 being particularly well-adapted for detecting ice on airplanes. In the system of FIG. 11, large sections of the airplane are scanned at one time whereas, in the system of FIG. 12, a polarized light beam illuminates locally the wing of the plane while a scanner is used to cover the desired area of the plane point-by-point. The scattered light collected passes through a polarizing beam splitter (or other polarization selection apparatus) to select the two polarization components and record their intensity. The polarized light coming from the free-of-ice aluminum wing will remain almost completely polarized whereas the ice-covered part of the wing will strongly depolarize the scattered light. The ratio of the parallel over perpendicular intensities for each point on the wing (I∥/I⊥) is calculated. When the ratio is high, i.e. much greater than 1, the wing is free of ice. When the ratio is nearly 1, i.e., between 1 and 2, then there is ice on this part of the wing. Instead of using the ratio (I∥/I⊥), one may choose to use other functions such as [I∥–I⊥], [I∥–I⊥]/[I∥+I⊥], [I⊥]/[I∥–I⊥], [I∥–I⊥]/[I⊥] and [I∥]/[I∥–I⊥].

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. A method for imaging a turbid medium at a depth below the surface thereof, said method comprising the steps of:
   (a) illuminating the turbid medium with a first light of a first wavelength, the first light being polarized and having a first state of polarization, whereby said first light, after entering the turbid medium, emerges therefrom partially depolarized;
   (b) detecting a component of the partially depolarized first light that is normal to said first state of polarization;
   (c) illuminating the turbid medium with a second light of a second wavelength, said second wavelength being different from said first wavelength, the second light being polarized and having a second state of polarization, whereby said second light, after entering the turbid medium, emerges therefrom partially depolarized;
   (d) detecting a component of the partially depolarized second light that is normal to said second state of polarization; and
   (e) forming an image of the turbid medium using the normal components of the partially depolarized first and second lights.

2. The method as claimed in claim 1 wherein the turbid medium is a tissue sample.

3. The method as claimed in claim 1 wherein the illuminating light comes from a pulsed or continuous light source (lamp, laser).

4. The method as claimed in claim 1 wherein said image forming step is performed point-by-point or over an area using a photomultiplier or a photodiode or a CCD camera or an equivalent photodetector.

5. The method as claimed in claim 1 wherein the first and second lights are pulsed or continuous, laser source or any other light source operating in the spectral region between 400 and 1600 nm such as semiconductor laser, Ti:Sapphire laser (800–1000 nm), $Cr^{4+}$:Forsterite laser (1100–1350 nm) or $Cr^{4+}$:YAG (1300–1600 nm).

6. The method as claimed in claim 1 wherein the different wavelengths used are composed of spectral bands with different central wavelength of the band.

7. The method as claimed in claim 1 wherein the first and second wavelengths are appropriately chosen to enable the first and second lights, respectively, to reach different mean photon-visit depths in the turbid medium.

8. The method as claimed in claim 1 wherein each of said first and said second lights is linearly polarized and wherein said detecting steps comprise detecting the perpendicular components of the partially depolarized backscattered light from said first and second lights, respectively.

9. The method as claimed in claim 1 wherein said forming step comprises calculating a difference between the normal components of the partially depolarized first and second lights and using said difference to form an image of the turbid medium.

10. The method as claimed in claim 1 wherein said first light has a wavelength of about 570 nm and wherein said second light has a wavelength of about 600 nm.

11. The method as claimed in claim 1 wherein the delivery of the illuminating light and the light collection for image formation is performed using an endoscope or similar system.

* * * * *